(12) United States Patent
Vitali et al.

(10) Patent No.: US 7,613,507 B2
(45) Date of Patent: Nov. 3, 2009

(54) NON-INVASIVE DETECTION OF THE OCCURRENCE OF APNEAE OR HYPOPNEAE IN A PATIENT

(75) Inventors: Luca Vitali, Strambino (IT); Elodie Vincent, Antony (FR)

(73) Assignee: ELA Medical S.A.S., Montrouge (FR)

( * ) Notice: Subject to any disclaimer, the term of this patent is extended or adjusted under 35 U.S.C. 154(b) by 401 days.

(21) Appl. No.: 11/428,798

(22) Filed: Jul. 5, 2006

(65) Prior Publication Data
US 2007/0167851 A1 Jul. 19, 2007

(30) Foreign Application Priority Data
Jul. 5, 2005 (FR) .................................. 05 07121
Apr. 20, 2006 (FR) .................................. 06 03484

(51) Int. Cl.
*A61B 5/04* (2006.01)
(52) U.S. Cl. .................. 600/509; 600/513; 600/529
(58) Field of Classification Search ................. 600/509, 600/513, 595
See application file for complete search history.

(56) References Cited

U.S. PATENT DOCUMENTS

| | | | |
|---|---|---|---|
| 5,304,208 A | 4/1994 | Inguaggiato et al. | |
| 5,496,351 A | 3/1996 | Plicchi et al. | |
| 6,551,252 B2 * | 4/2003 | Sackner et al. | 600/536 |
| 6,574,507 B1 | 6/2003 | Bonnet | |
| 2004/0006375 A1 | 1/2004 | Poezevera | |
| 2004/0111038 A1 | 6/2004 | Salla et al. | |
| 2004/0138718 A1 | 7/2004 | Limo'usin et al. | |
| 2004/0176695 A1 | 9/2004 | Poezevara | |
| 2005/0085738 A1 * | 4/2005 | Stahmann et al. | 600/529 |
| 2005/0131470 A1 | 6/2005 | Vitali | |
| 2005/0137488 A1 | 6/2005 | Henry | |

(Continued)

FOREIGN PATENT DOCUMENTS

EP 1336422 8/2003

(Continued)

OTHER PUBLICATIONS

Floyd B. Willis, MD, Amber L. Isley, MD, Yonas E. Geda, MD, MSc, Luther Quarles, IV, and Paul A. Frederickson, MD. "Resolution of Syncope With Treatment of Sleep Apnea." The Journal of the American Board of Family Medicine, vol. 21, No. 5 (Sep.-Oct. 2008): 466-468.*

*Primary Examiner*—Mark W Bockelman
*Assistant Examiner*—Elizabeth K So
(74) *Attorney, Agent, or Firm*—Orrick Herrington & Sutcliffe, LLP

(57) ABSTRACT

A device for the non-invasive detection of apneae or hypopneae in a patient. This apparatus collects the patient's endocardial acceleration using an external acceleration sensor (12) able to be maintained in contact with the patient's thoracic wall (10). An analysis is made to determine at least one parameter that is function of collected endocardial acceleration and to conditionally deliver an apnea or hypopnea alert signal as a function of the value taken by this parameter. This parameter can notably be a function of one and/or the other of the two endocardial acceleration peaks over one given heart cycle, the first peak (PEA I) corresponding to the ventricular isovolumetric contraction phase and the second peak (PEA II) to the ventricular isovolumetric relaxation phase.

24 Claims, 2 Drawing Sheets

U.S. PATENT DOCUMENTS

2006/0189874 A1   8/2006   Vitali et al.

FOREIGN PATENT DOCUMENTS

| | | |
|---|---|---|
| EP | 1413330 | 4/2004 |
| EP | 1433496 | 6/2004 |
| EP | 1533001 | 5/2005 |
| EP | 1537894 | 6/2005 |
| EP | 1674035 | 6/2006 |

* cited by examiner

NON-INVASIVE DETECTION OF THE OCCURRENCE OF APNEAE OR HYPOPNEAE IN A PATIENT

FIELD OF THE INVENTION

The present invention is directed to an apparatus for non-invasive detection of the occurrence of apneae or hypopneae in a patient.

BACKGROUND OF THE INVENTION

In a general manner, the respiratory pathology known as "Sleep Apnea Syndrome" (SAS) is characterized by the frequent occurrence (at least 10 to 20 times per hour) of apneae during a sleep phase of the patient. An "apnea" (or respiratory pause) is defined as a temporary stop of the respiratory function, with a duration longer than 10 seconds. SAS can also be characterized by the occurrence of hypopneae under the same conditions. A "hypopnea" is defined as a significant decrease (but with no interruption) of breathing airflow, typically a decrease of more than 50% as compares to an average of preceding airflow.

Facing this pathology, what affects more than 4% of the population, and more than 50% of the patients suffering from heart failure, the autonomic nervous system becomes adapted, but with a noxious effect on sleep, to the interruption or reduction of breathing airflow leading to a decrease of the blood oxygen concentration, as well as unconscious micro-awakenings. That is followed, during arousal, by diurnal sleepiness with a loss of attention and increased risks of road accidents. Moreover, the physiologic, then pathologic, adaptive response of certain organs including the heart and respiratory system leads to a greater incidence of such disorders as arterial hypertension, ventricular arrhythmiae, myocardial infarction and heart failure.

Diverse techniques intended to detect sleep respiratory disorders by means of an implantable device are known in the prior art.

European patent EP 0970713 and its U.S. patent counterpart U.S. Pat. No. 6,574,507 (commonly assigned herewith to ELA Medical) discloses a device that diagnoses the occurrence of an apnea based upon a signal representing minute ventilation (VE signal, or MV signal), a preponderantly physiological parameter, usually obtained through a measurement of transthoracic impedance, providing a continuous indication of the patient's respiratory rhythm.

One drawback of this technique relates to the fact it requires that the patient be implanted with a device, which is a limit to the usefulness and effectiveness of this technique.

OBJECTS AND SUMMARY OF THE INVENTION

This invention proposes a new approach in the diagnosis of the pathologies of respiratory activity, by means of an external apparatus, therefore non invasive, which can easily be placed onto the patient, and which does not induce any discomfort comparable to that induced by certain devices implementing respiratory masks that shall be worn during the sleep.

It is therefore, an object of this present invention is to propose to the physicians such an apparatus that is simple to operate and non-invasive (therefore applicable to any patient, should he/she be or not implanted with a device) and that provides to the physician, not only rough data, but also an aid to diagnosis, notably based upon the criteria that led to the diagnosis of apneae or hypopneae.

Essentially, the invention proposes a detection of apneae or hypopneae based upon the measurement of endocardial acceleration, more precisely based upon the analysis of peaks of endocardial acceleration, which is a parameter reflecting in a non-artifacted way, and with a very low response time, of the variations of myocardial contractility.

So as to obtain a better detection of pathologic respiratory events, this endocardial acceleration signal can be analyzed, in the alternative, in cross-reference with some other physiologic signals such as heart rate.

One already knows from the prior art, see, for example, European Published Patent Application EP-A-1413330 and its counterpart Published Patent Application U.S. 2004/0138718 (assigned herewith to ELA Medical), a device comprising means for measurement of endocardial acceleration and able to diagnose and treat respiratory disorders. However this patent disclosure concerns with an implantable device of the pacemaker type, which can therefore only be implemented under specific conditions and concerns a limited population of patients. Also, the device described by that document is analyzing ventilatory activity and is detecting the occurrence of apneae or hypopneae by analyzing the signal provided by a minute ventilation sensor based upon measurement of intrathoracic impedance. That latter device does not use endocardial acceleration for diagnosing apneae or hypopneae, but only to adapt the therapy (modulation of pacing rate) applied to the patient once the apnea or hypopnea has been detected.

So as to allow a non-invasive detection of the occurrence of apneae or hypopneae, one aspect of the invention is directed to a device comprising means for collecting the patient's endocardial acceleration, comprising an external acceleration sensor able to be maintained in contact with the patient's thoracic wall, and means for analysis, able to determine at least one parameter that is function of said collected endocardial acceleration and to conditionally deliver an apnea or hypopnea alert signal as a function of the value taken by said at least one parameter.

Preferably, the parameter is at least one parameter that is function of one and/or the other of two endocardial acceleration peaks occurring over it's given cardiac cycle, these two peaks comprising a first peak during ventricular isovolumetric contraction phase (PEA I) and a second peak during the ventricular isovolumetric relaxation phase (PEA II). The said at least one parameter can notably be function of (i) an average value of one or both peaks over a number of cycles, and/or (ii) a variation of one or both peaks over a number of cycles, and/or (iii) a difference or ratio between a long-term average and a short term average of the value of endocardial acceleration peak(s) collected over a plurality of successive cycles. As an alternative, the parameter can also be a function of the interval between QRS complex and at least one of the endocardial acceleration peaks, and/or of the interval between the first and second peak of endocardial acceleration in a given cycle.

The means for analysis can comprise means able to compare the parameter(s) to a predetermined threshold, and deliver the alert signal when this threshold is crossed.

In a particular embodiment of the invention, the parameter is function of a ratio between a long term average and a short term average of the values of endocardial acceleration peak(s) collected over a plurality of successive cycles, and the means for analysis comprise means for comparing this ratio to a first predetermined threshold and deliver the alert signal when this threshold is crossed.

Preferentially, the alert signal can be delivered after crossing the first threshold only if the latter remains crossed during a predetermined minimum duration, or over a predetermined number of heart cycles.

In addition, in one preferred embodiment, the means for analysis can further comprise means able to, after crossing said first threshold, detect a reverse crossing of said first threshold followed by crossing a second threshold, higher than the first; and means to deliver a signal of confirmation of the apnea or hypopnea episode when the second threshold is crossed. This confirmation signal is preferentially delivered only if crossing of the second signal occurs during a predetermined maximum duration, or during a predetermined maximum number of heart cycles, after reverse crossing of the first threshold.

In alternative or in addition, the means for analysis can comprise a state machine or neuronal network able to compare a plurality of parameters to a plurality of predetermined thresholds, to detect crossing of the different thresholds, analyze the sequence of crossings and to deliver said alert signal upon detection of one or more predetermined sequences of crossings.

One can also look into means for applying to endocardial acceleration: an autocorrelation function, morphologic analysis, frequential analysis, wavelet analysis, and/or principal components analysis.

Advantageously, the apparatus also comprises means for collecting at least one physiological data among: heart rate, nasal pressure and/or blood oxygen saturation of the patient, and the means for analysis are able to conditionally deliver the alert signal as a function of both said at least one physiological data and the value taken by said at least one parameter.

BRIEF DESCRIPTION OF THE DRAWINGS

Further characteristics, features and advantages of the present invention will become apparent to a person of ordinary skill in the art in view the following detailed discussion of preferred embodiments of the present invention, made with reference to the drawings annexed, in which.

Figure 1:
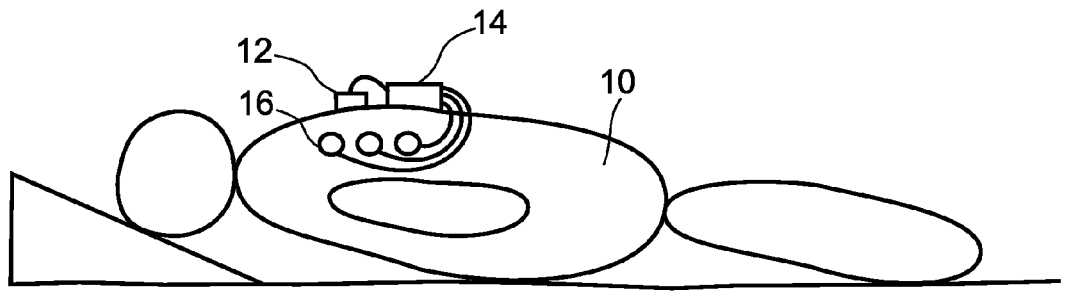
FIG. 1 is a schematic showing the apparatus of the invention connected to a recumbent patient.

On FIG. 1 reference 10 represents a recumbent patient, for whom it is wished to diagnose sleep disorders. In a manner characteristic of the invention, the patient is equipped with an external acceleration sensor 12 placed in the sternum vicinity and maintained applied against the thoracic wall, for example (but in a non-limitative manner), by means of a "patch" such as that used for maintaining ECG electrodes, the whole being eventually covered by an adhesive strip. As it can be seen, the implementation of the apparatus of the invention is particularly simple and non-invasive, as it only requires to apply the acceleration sensor against the patient's thoracic wall. Moreover, for the patient, it does not induce any additional discomfort comparing to the wearing of a Holter recorder, a technique which is commonly used for other types of ambulatory diagnosis.

The sensor 12 is connected to a recording device 14, for example, a Holter recorder able to record throughout a long duration (at least the duration of the sleep period), the signals provided by the sensor, and to process and convert those so as to derive the information necessary for the diagnosis of apneae and hypopneae.

The patient can also be equipped with electrodes 16 for collecting surface ECG, connected to the recorder 14 as well, allowing in particular to obtain a heart rate signal with which the information provided by the acceleration sensor 12 can be combined.

Figure 2:
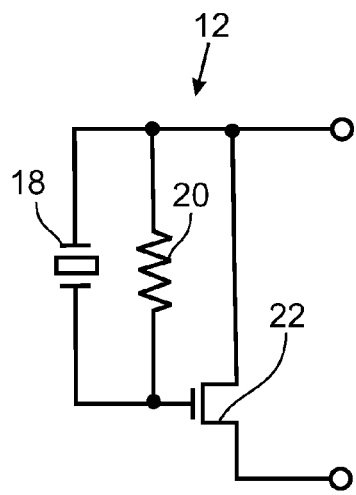
FIG. 2 is a schematic circuit for the accelerometer of FIG. 1.
Figure 3:
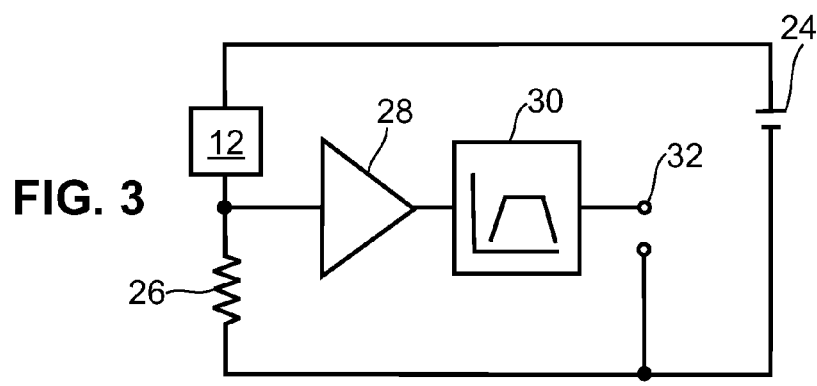
FIG. 3 is a schematic circuit of the input and shaping of the signal delivered by the accelerometer of FIG. 2.

FIG. 2 shows more details of a preferred structure of acceleration sensor 12, which comprise a sensitive piezoelectric component 18 polarized by a resistance 20 and associated to a preamplification MOS transistor 22. As it can be seen on FIG. 3, the sensor 12 is polarized by a voltage source 24 in series with a resistance 26. The output signal of the sensor 12 is amplified by an amplifier 28, then shaped by a passband filter 30 and delivered to the output 32 for subsequent digitalizing and processing.

Figure 4:
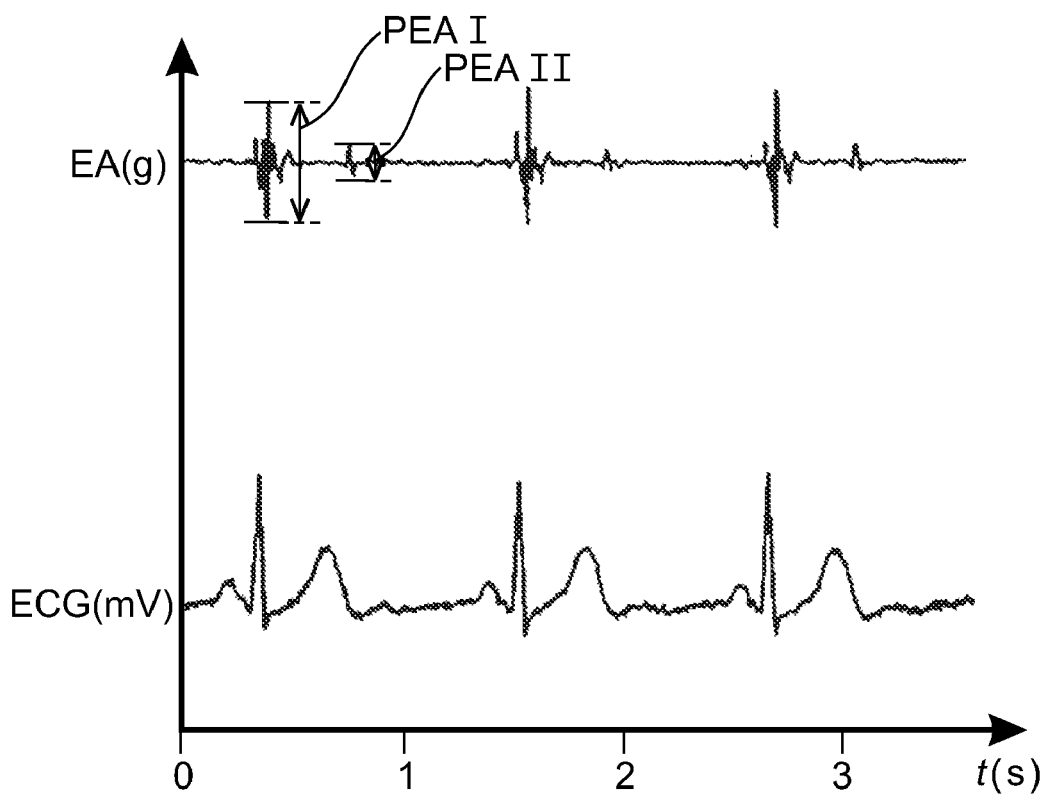
FIG. 4 is a time diagram showing the representative variations, over three successive heart cycles, of endocardial acceleration, and a corresponding electrogram and surface electrocardiogram.

The top curve illustrated on FIG. 4 shows the variations of endocardial acceleration (EA), measured by a sensor such as that described in EP 0515319 and its US counterpart patent U.S. Pat. No. 5,304,208 (assigned to Sorin Biomedico Cardia SpA), which is incorporated hereby reference, integrated at the tip of an endocardial lead placed in the fundus of the ventricle. FIG. 4 also shows the electrogram (EGM) trace, i.e., the electrical signal collected by the distal electrode of this sensor, and corresponding surface electrocardiogram (ECG), over three successive heart cycles.

The endocardial acceleration signal measured over one heart cycle presents, among other things, two peaks corresponding to the two main noises that can be identified in each beat of a healthy heart. EP 0655260 and its U.S. patent counterpart U.S. Pat. No. 5,496,351 (commonly assigned herewith to Sorin Biomedica Cardio SpA) describes a technique for processing endocardial acceleration signal provided by the sensor at the tip of the lead, so as to derive, notably, these two values of endocardial acceleration peaks, particularly useful for detecting heart disorders, and for triggering or not a defibrillation therapy.

The term "peak" hereafter refers to the maximum peak-to-peak value of the acceleration signal separating the two extrema, positive and negative, corresponding to the variances PEA I and PEA II shown on the time diagram of FIG. 4. More precisely, the first endocardial acceleration peak ("PEA I") corresponds to the closure of mitral and tricuspid valves, at the beginning of the phase of isovolumetric ventricular contraction (systole). The variations of this first peak are closely related to pressure variations in the ventricle (the amplitude of PEA I peak, being more precisely correlated to the positive maximum of pressure variation, dP/dt, in the left ventricle) and can therefore constitute a representative parameter for myocardium contractility, being itself correlated to the level of activity of the sympathetic system. The second peak of endocardial acceleration ("PEA II") corresponds to the closure of aortic and pulmonary valves, during the phase of isovolumetric ventricular relaxation. That second peak, which is produced by the brutal deceleration of moving blood mass in the aorta, constitutes a representative parameter for peripheral blood pressure at the beginning of the diastole. It also constitutes a key-parameter of the physiologic process leading to the occurrence of a vasovagal syncope.

The values of PEA I and/or PEA II are collected over successive cycles, optionally as well the heart rate.

These signals can be processed through different techniques.

A first technique consists of determining, cycle to cycle, the absolute values taken by these parameters, and to set alert-triggering threshold—or, preferentially, determine an averaged value of these parameters over a predetermined number of cycles, so as to avoid any influences from cycle-to-cycle variability (dispersion of measurements) and from non-significant brief events.

In order to determine the presence or absence of apnea or hypopnea, one or more thresholds are set, and each of the parameters PEA I or PEA II (or a combination of these two parameters) is compared to a corresponding predetermined threshold. The result of this comparison can be combined in different ways with the result of similar comparisons between other parameters (notably the heart rate) in order to provide an output signal with two states, one of the states being associated with a normal situation, and the other state being associated with an apnea or hypopnea alert.

In order to improve the specificity of detection, and notably to take into account the differences in basic values of PEA parameters from one patient to another, one can advantageously analyze the variations of these parameters, rather than absolute values.

Yet another way to proceed concerns analyzing the difference between a short term average and long term average of the same parameter. If this parameter does not vary much, the difference will be low and the two values will tend to coincide. Reciprocally, as soon as the parameter becomes unstable, the short-term average will follow the variations of the parameter more rapidly than the long-term average. Then the difference between the two averages will no longer be null or close to null, but will have a positive value (in case of increase of the parameter) or negative value (in case of decrease), the absolute value of this variance being dependent upon the analyzed parameter and the rate of change thereof.

It is also possible to follow the ratio between short-term and long-term average of PEA I and/or PEA II parameters, instead of following the difference.

An example of algorithm for apnea detection consists of calculating a short-term moving average of cycle-to-cycle values of PEA I parameter, for example over 4 consecutive cycles. Simultaneously, a long-term moving average, for example over 500 cycles, of this same parameter is calculated and updated. The two averages are then compared so as to provide a ratio R, with R=short-term average/long-term average. Preferably, the number of cycles in the long term average is at least one and more preferably about two orders of magnitude greater than the number of cycles in the short term average.

Figure 5:
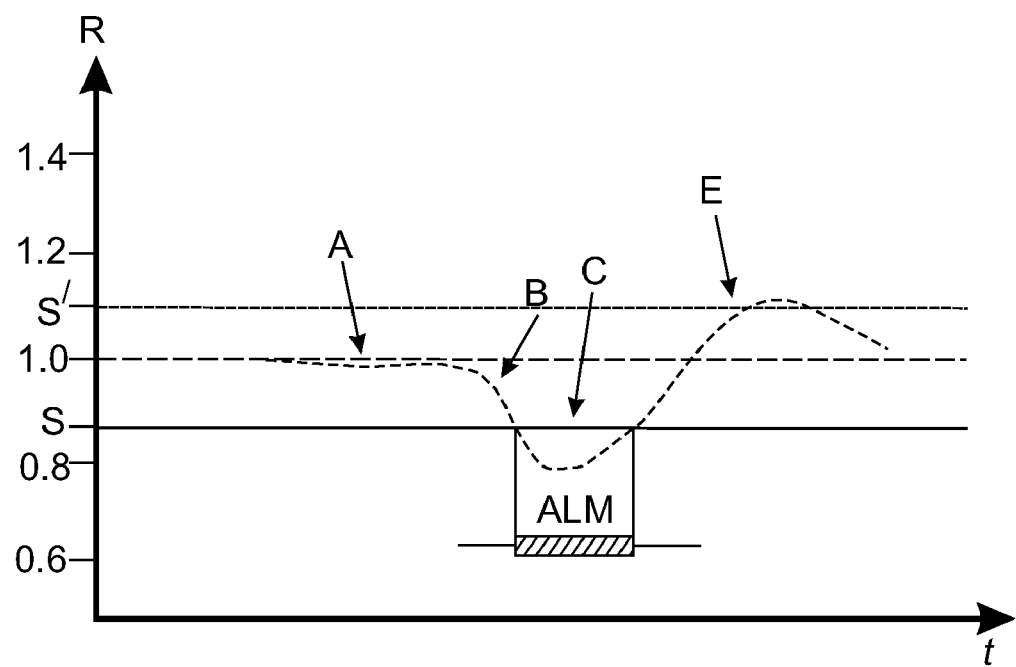
FIG. 5 shows the variations of the ratio between a short term average and a long term average of endocardial acceleration during a typical apnea episode.

The variations of this ratio R are illustrated by FIG. 5: In steady state, the ratio R has an relatively constant value close to 1. On the other hand, during an apnea episode, the diminution of blood oxygen saturation induces a reduction of cardiac contractility that is translated by a corresponding decrease of the amplitude of PEA I parameter over a number of consecutive beats, and therefore a correlative decrease of the value of the ratio R. That situation is illustrated by FIG. 5, where A represents the beginning of the apnea episode and B corresponds to the moment when endocardial acceleration dramatically drops down following the reduction of contractility.

It is possible to trigger an alert (i.e., an alarm) by defining a threshold S that is appropriate for ratio R, for example S=0.85 or S=0.9, and by comparing the current value of ratio R to that threshold. Each time the ratio R falls below that threshold (illustrated by C on FIG. 5), an alert or alarm (ALM) is triggered. This alarm can be triggered immediately, at the moment the threshold is crossed, or more preferably in a conditional manner, for example, only if the ratio R remains below the threshold during a minimum predetermined duration (for example, 5 seconds), or over a predetermined minimum number of cycles (for example, 5 cycles).

Triggering of the alarm therefore indicates an episode of sudden depression of cardiac contractility, that is associated to an apnea (or hypopnea) episode. That triggers in response, the storage into a memory of the recorder 14, of diagnosis information such as a marker of apnea occurrence, timestamping of this apnea, duration of the alarm, etc. It is also possible to simultaneously record the endocardial acceleration signals and/or the values of the different PEA parameters. This storage can eventually be triggered following certain programmed conditions, or upon detection of certain status (confirmed sleep) or events (occurrence of an apnea episode). The stored signals can postrequisitely be visualized by a physician equipped with a programmer able to read the device's memory contents. It can also be possible, at this point, to analyze the PEA signal in order to extract certain parameters that are not determinable in real-time, such as sinus variability, or to simulate the application of detection algorithms in order to choose the one that is the most appropriate to the patient.

Moreover, one usually observes after the end of the apnea episode, a phenomenon of rebound, corresponding to a transitory increase of cardiac contractility (this rebound is illustrated by E on FIG. 2). More precisely, in the end of an apnea episode, a microwakening often occurs, during which the sympathetic system is activated in reaction to previous events; that reaction spontaneously ends after a certain number of heart cycles, the ratio R progressively returning to its basic value close to 1.

That phenomenon of rebound can be detected and utilized so as to confirm the occurrence of the apnea episode. To that end, a second threshold S' is defined, with a value higher than 1, for example S'=1.1, and the crossing of this second threshold S' is detected after detection of an apnea episode. It shall be noted that crossing of the threshold S' simply reveals a positive reaction of sympathetico-vagal system whose state is abnormal due to the apnea, that reaction being not pathologic per se, and shall not trigger the alarm nor any particular therapy.

However, the joint detection of (i) a diminution of PEA revealing a reduction of contractility, detected by crossing of the first threshold S (ratio R<0.85), followed by (ii) an increase of PEA, detected by crossing of the second threshold (ratio R>1.1), that occurs (iii) within a predetermined time interval, for example, over a time interval of one minute, is a strong index of a non-physiologic state typically encountered in patients suffering from sleep disorders. The detection of such a typical profile of PEA variation can be utilized to calculate a specific index, allowing to diagnose in the patient the presence or absence of instability of sympathetico-vagal system.

In addition, it is possible to take into account the PEA II parameter as an alternative or addition to PEA I for the detection of apneae as described above. PEA II can be utilized as an indicator for a reduced contractility, insofar as it is correlated to the variations of blood pressure. More precisely, a reduced contractility combined with a slowing-down of heart rhythm induces a diminution of blood pressure that is translated by a reduction of PEA II amplitude. The analysis of this parameter thus allows confirming apnea episodes.

Some other types of analyses, more complex, can also be implemented in order to further refine the reliability of the detection process. For instance, techniques of correlation, morphology analysis of the signal, frequantial analysis, wavelet analysis, principal components analysis, etc., can be used.

It is also possible to use a process of the "state machine" type, in which the results of the comparisons of different parameters to different thresholds are applied to a state transition system with memory management, which takes the decision to trigger an apnea or hypopnea alert as a function of a more complex evolution scheme.

One can further look into an auto-adaptive system, i.e., a system able to adapt to long term variations, in order to subsequently adjust the specificity of the detection system.

Finally, it is possible to combine this analysis of PEA with a parallel analysis of heart rate, in order to improve sensitivity and specificity of the detection and classification of apnea episodes. Indeed, heart rate is decreasing at the beginning of the respiratory event and is increasing at the moment of the micro-wakening that follows the event, or presents a characteristic variability during the occurrence of the event.

In order to improve the diagnosis, it is also possible to combine the analysis of the PEA to the analysis of a nasal pressure signal, for example collected by means of a pressure sensor via a nasal canula, or the analysis of a signal from a blood oxygen saturation sensor.

One skilled in the art will appreciate that the present invention can be practiced by other than the described embodiments, which are presented for purposes of illustration and not of limitation.

We claim:

1. A device for non-invasive detection of the occurrence of apnea or hypopnea in a patient, comprising:
    means for collecting the patient's endocardial acceleration, comprising an external acceleration sensor able to maintain contact with the patient's thoracic wall, and
    means for analysis, able to:
        determine at least one parameter value by evaluating a function of a ratio of a long term average of the values of the endocardial acceleration peaks to a short term average of the values of endocardial acceleration peaks collected over a plurality of successive cycles;
        compare the at least one parameter value to a first predetermined threshold; and
        deliver an apnea or hypopnea alert signal in response to the at least one parameter value crossing the first predetermined threshold.

2. The device of claim 1, wherein said at least one parameter value is function of at least one of a first endocardial acceleration peak (PEA I) during the isovolumetric ventricular contraction phase and a second endocardial acceleration peak (PEA II) during the isovolumetric ventricular relaxation phase.

3. The device of claim 2, further comprising means for non-invasively detecting the patient's electrocardiogram wave form including a QRS complex wherein said function of said at least one parameter is an interval between a QRS complex and at least one of the two endocardial acceleration peaks, and/or the time interval between said first and second endocardial acceleration peaks.

4. The device of claim 1, wherein the means for analysis can deliver said alert signal after crossing of said first threshold only if said first threshold remains crossed during one of a predetermined minimum duration and a predetermined minimum number of heart cycles.

5. The device of claim 1, wherein the means for analysis further comprises means able, after crossing of said first threshold, to detect a reverse crossing of said first threshold followed by crossing of a second threshold, said second threshold being higher than the first threshold, and to deliver a signal of confirmation of the apnea or hypopnea episode at the crossing of this second threshold.

6. The device of claim 5, wherein the means for analysis can deliver said signal of confirmation of apnea or hypopnea episode only if the crossing of said second threshold occurs during one of a predetermined maximum duration and a predetermined maximum number of heart cycles, following said reverse crossing of said first threshold.

7. The device of claim 1, wherein the means for analysis further comprises a state machine or neuronal network able to compare a plurality of said parameters to a plurality of predetermined thresholds, to detect the crossing of the predetermined thresholds, to analyze the sequence of the crossings and deliver an alert signal upon detection of a predetermined sequence of crossings.

8. The device of claim 1, wherein the means for analysis comprises means able to apply an autocorrelation processing, a morphologic analysis, a frequental analysis, a wavelet analysis and/or a principal components analysis to an endocardial acceleration.

9. The device of claim 1, further comprising means for collecting at least one physiologic data among: heart rate, nasal pressure and/or blood oxygen saturation of the patient, and in which the means for analysis are means able to conditionally deliver the alert signal as a function of both said at least one physiologic data and the value taken by said at least one parameter.

10. A device for non-invasive detection of the occurrence of apnea or hypopnea in a patient, comprising:
    means for collecting the patient's endocardial acceleration comprising an external acceleration sensor able to maintain contact with the patient's thoracic wall;
    means for determining at least one parameter value by evaluating a function of a ratio between a long term average of the values of the endocardial acceleration peaks to a short term average of the values of endocardial acceleration peaks collected over a plurality of successive cycles;
    means for comparing the at least one parameter to a first threshold; and
    means for delivering an alert signal corresponding to an apnea or a hypopnea in response to the at least one parameter value crossing the first predetermined threshold.

11. The device of claim 10 wherein said function further comprises an average of said at least one parameter value over a plurality of successive cycles.

12. The device of claim 10 wherein said function further comprises a variation of said at least one parameter value over a plurality of successive cycles.

13. The device of claim 10 wherein said at least one parameter value is a function of an endocardial acceleration peak (PEA I) measured during the isovolumetric ventricular contraction phase.

14. The device of claim 10 further comprising means for non-invasively detecting a QRS complex in said patient's electrocardiogram, wherein said at least one parameter value is a function of an interval between a QRS complex and said endocardial acceleration peaks.

15. The device of claim 10 wherein said at least one parameter value is a function of an endocardial acceleration peak (PEA II) measured during the isovolumetric ventricular relaxation phase.

16. The device of claim 15 further comprising means for non-invasively detecting a QRS complex in said patient's electrocardiogram wherein said at least one parameter value is a function of an interval between a QRS complex and said endocardial acceleration peaks.

17. The device of claim 10 wherein said at least one parameter is a function of a time interval between a first endocardial acceleration peak measured during the isovolumetric ventricular contraction phase and a second endocardial acceleration peak measured during the isovolumetric relaxation phase.

18. The device of claim 10, wherein the means for delivering said alert signal further comprises means for delivering said alert signal in response to said first threshold remaining crossed during a predetermined minimum duration, or over a predetermined minimum number of heart cycles.

19. The device of claim 10, wherein the means for delivering an alert signal further comprises means for detecting, after crossing of said first threshold, a reverse crossing of said first threshold followed by crossing of a second threshold, higher than said first threshold, and means for delivering a signal of confirmation of an apnea or hypopnea episode in response to said crossing of this second threshold.

20. The device of claim 19, wherein the means for delivering said signal of confirmation operates only if the crossing of said second threshold occurs during one of a predetermined maximum duration and a predetermined maximum number of heart cycles, following said reverse crossing of the first threshold.

21. The device of claim 10, further comprising means for non-invasively collecting the patient's heart rate, wherein said means for delivering said alert signal is able to conditionally deliver said alert signal as a function of both the patient's heart rate and at least one parameter value.

22. The device of claim 10 further comprising means for non-invasively collecting the respiratory activity, able to provide a signal of said patient's ventilatory activity, and wherein said means for delivering said alert signal is as a function of both the patient's ventilatory activity signal and the at least one parameter value.

23. The device of claim 10 further comprising means for detecting at least one phase of exercise and/or sleep, and providing a signal corresponding to the patient's status indicative of whether the patient is in a sleep phase or an exercise phase, and the means for delivering said alert signal is able to conditionally deliver the alert signal as a function of both the patient's status signal and the at least one parameter value.

24. The device of claim 10, wherein the at least one parameter value further comprises a plurality of parameters values, and said threshold further comprises a plurality of predetermined thresholds, said device further comprising a state machine or neuronal network able to compare said plurality of said parameters values to said plurality of predetermined thresholds, to detect the crossing of the different thresholds, to analyze any sequence of these crossings and to deliver said alert signal upon detection of one or more predetermined sequence(s) of crossings.

* * * * *